United States Patent [19]

Poittevin et al.

[11] 4,053,618
[45] Oct. 11, 1977

[54] THIAZOLE ALKANOIC ACIDS, HYPOLIPEMIANT COMPOSITIONS CONTAINING THEM AND METHODS OF INDUCING HYPOLIPEMIC ACTIVITY UTILIZING THEM

[75] Inventors: Andre Poittevin, Vaires-sur-Marne; Vesperto Torelli, Maisons-Alfort, both of France

[73] Assignee: Roussel-UCLAF, Paris, France

[21] Appl. No.: 654,514

[22] Filed: Feb. 2, 1976

[30] Foreign Application Priority Data

Dec. 12, 1975  France .................................. 75.38061

[51] Int. Cl.² .................. A61K 31/425; C07D 277/30; C07F 5/06
[52] U.S. Cl. .................................. 424/270; 260/299; 260/302 R
[58] Field of Search .......................... 260/299, 302 R; 424/270, 245

[56] References Cited

U.S. PATENT DOCUMENTS

| | | | |
|---|---|---|---|
| 3,749,787 | 7/1973 | Hepworth et al. | 424/270 |
| 3,882,110 | 5/1975 | Clemence et al. | 260/247.1 M |
| 3,925,399 | 12/1975 | Clemence et al. | 260/299 |

FOREIGN PATENT DOCUMENTS 2,162,468  6/1972  Germany

OTHER PUBLICATIONS

Garraway, Chemical Abstracts, v. 81, 73,315p (1974).

Primary Examiner—Donald G. Daus
Assistant Examiner—Diana G. Rivers
Attorney, Agent, or Firm—Hammond & Littell

[57] ABSTRACT

Novel thiazole derivatives of the formula

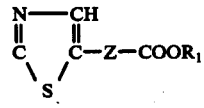

wherein R is alkyl of 1 to 5 carbon atoms, Z is selected from the group consisting of —CH=CH—, —CH=CH—CH=CH— and $(CH_2)_n$—, $n$ is an integer from 1 to 6 and $R_1$ is selected from the group consisting of hydrogen, alkyl of 1 to 5 carbon atoms, —NH₄ and alkali metal, alkaline earth metal and aluminum cations and the non-toxic, pharmaceutically acceptable acid addition salts thereof which have antilipolytic activity and are useful intermediates and their preparation and intermediates produced therein.

15 Claims, No Drawings

THIAZOLE ALKANOIC ACIDS, HYPOLIPEMIANT COMPOSITIONS CONTAINING THEM AND METHODS OF INDUCING HYPOLIPEMIC ACTIVITY UTILIZING THEM

STATE OF THE ART

Zubarovskii et al [Chem. Ab., Vol. 58 (1963), p. 2525b] describes the preparation of 2-methyl-thiazole-5-methanol by reaction of ethyl 2-methyl-thiazole-5-carboxylate with lithium aluminum hydride but does not describe any pharmacological properties therefor.

Copending, commonly assigned U.S. Patent Application Ser. No. 495,556 filed Aug. 8, 1974, now U.S. Pat. No. 3,957,809, describes novel thiazole derivatives of the formula

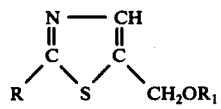

wherein R is alkyl of 2 to 12 carbon atoms and $R_1$ is selected from the group consisting of hydrogen, alkyl of 1 to 8 carbon atoms and acyl of an organic carboxylic acid of 1 to 12 carbon atoms having hypolipemiant activity with a very prolonged vasodilatatory activity and their preparation.

OBJECTS OF THE INVENTION

It is an object of the invention to provide the novel thiazole derivatives of formula I and their acid addition salts and a process for their preparation and novel intermediates produced therein.

It is another object of the invention to provide novel hypolipemiant compositions.

It is a further object of the invention to provide a novel method of inducing hypolipemic activity in warm-blooded animals.

These and other objects and advantages of the invention will become obvious from the following detailed description.

THE INVENTION

The novel products of the invention are selected from the group consisting of thiazoles of the formula

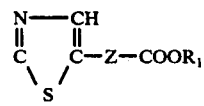

wherein R is alkyl of 1 to 5 carbon atoms, Z is selected from the group consisting of -CH=CH-, -CH=CH-CH=CH- and -$(CH_2)_n$-, n is an integer from 1 to 6 and $R_1$ is selected from the group consisting of hydrogen, alkyl of 1 to 5 carbon atoms, -$NH_4$ and alkali metal, alkaline earth metal and aluminum cations and the non-toxic, pharmaceutically acceptable acid addition salts thereof.

Examples of alkyl groups of 1 to 5 carbon atoms are methyl, ethyl, propyl, n-butyl, isobutyl, tert.-butyl and pentyl. Examples of suitable alkali metal and alkaline earth metal salts are the sodium, potassium and calcium salts.

Examples of suitable acids for the preparation of the non-toxic, pharmaceutically acceptable acid addition salts are strong mineral acids such as hydrochloric acid, hydrobormic acid, hydroiodic acid, nitric acid, sulfuric acid or phosphoric acid and strong organic acids such as alkylmonosulfonic acids and alkyldisulfonic acids like methanesulfonic acid, methanedisulfonic acid or α,β-ethanedisulfonic acid or arylmonosulfonic acids and aryldisulfonic acids like benzenesulfonic acid.

The invention has especially as object the products of formula I and their salts as defined above, wherein Z represents a group of formula -$(CH_2)_{n'}$- in which n' is an integer from 1 to 5.

Among the preferred products of formula I are those where Z is -$CH_2$-$CH_2$- , $CH_2$-$CH_2$-$CH_2$-$CH_2$-$(CH_2)_6$-, -CH=CH- and -C=CH-CH=CH- and their non-toxic, pharmaceutically acceptable acid addition salts thereof and the alkali metal, alkaline earth metal and aluminum salts thereof. More preferred are the compounds wherein Z is -$CH_2$-$CH_2$- and -$(CH_2)_4$-.

Among the preferred specific compounds are 2-methyl-5-thiazole-propanoic acid, 2-methyl-5-thiazole-pentanoic acid, 3-(2-methyl-5-thiazolyl)-2-propenoic acid, 5-(2-methyl-5-thiazolyl)-2, 4-pentadienoic acid, ethyl 5-(2-propyl 5-thiazolyl)2,4-pentadienoate and the hemi-α,β-ethane disulfonate of 2-propyl-5-thiazole-pentanoic acid.

The novel process of the invention for the preparation of compounds of formula I wherein Z is -$(CH_2)_n$- and n has the above definition comprises reaching an alkylthioamide of the formula

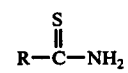

wherein R has the above definition with a compound of the formula:

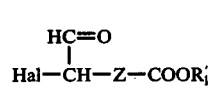

wherein Hal is bromine or chlorine, Z has the above definition and $R_1'$ is alkyl of 1 to 5 carbon atoms to obtain the corresponding compound of formula I wherein $R_1$ is alkyl of 1 to 5 carbon atoms which may be hydrolyzed to the free acid of formula I which may be reacted with an alkanol of 1 to 5 carbon atoms to form the corresponding ester.

The novel process of the invention for the preparation of compounds of formula I wherein Z is -CH=CH- or -CH=CH-CH=CH- comprises reacting a compound of the formula

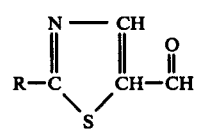

with either malonic acid in the presence of a basic agent to obtain a compound of formula I wherein Z is -CH=CH- and $R_1$ is hydrogen which may be esterified with an alkanol of 1 to 5 carbon atoms or with an alkyl dialkylphosphonocrotonate of the formula $$\begin{array}{c} \text{AlKO} \quad \text{O} \\ \diagdown \, \| \\ \quad \text{P—CH}_2\text{—CH=CH—COOR}_1' \\ \diagup \\ \text{AlKO} \end{array} \quad \text{V}$$

wherein AlK is alkyl of 1 to 3 carbon atoms and $R_1'$ has the above definition to obtain the corresponding compound of formula I wherein Z is -CH=CH-CH=CH- and $R_1$ is alkyl of 1 to 5 carbon atoms which may be hydrolyzed to the free acid of formula I which may be subsequently esterified with a lower alkanol.

The reaction of the compounds of formulae II and III is preferably effected in an organic solvent such as dichloroethane, benzene, toluene, dioxane, tetrahydrofuran or ethyl ether and is effected at reflux temperatures. The hydrolysis of the ester is preferably effected in the presence of an alkaline agent such as sodium hydroxide or potassium hydroxide. Any esterification is preferably effected in the presence of an acid such as hydrochloric acid or p-toluene sulfonic acid.

The reaction of the compound of formula IV with malonic acid is preferably effected in an organic solvent such as pyridine or collidine in the presence of a strong base such as piperidine or triethylamine. The resulting free acid of formula I may be esterified as described above.

The reaction of the product of formula IV with the alkyl dialkylphosphonocrotonate of formula V is preferably effected in the presence of a base like alkali metal hydrides such as sodium hydride or potassium hydride or alkali metal alcoholates such as potassium tert.-amylate or potassium tert.-butylate in an organic solvent such as benzene, toluene or tetrahydrofuran. The hydrolysis of the resulting ester may be effected as described above as well as any subsequent esterification.

The non-toxic, pharmaceutically acceptable acid addition salts may be prepared by reacting the compound of formula I with a strong mineral or organic acid preferably in an organic solvent such as ethylacetate, chloroform or methylene chloride.

The salts of the free acids of formula I wherein $R_1$ is hydrogen may be prepared by reacting the acid with a mineral or organic base such as sodium hydroxide, potassium hydroxide, calcium hydroxide, aluminum hydroxide, sodium ehtylate or potassium ethylate in the presence of at least one solvent such as water, ethyl ether, ethanol or acetone. The said salts may also be prepared by saponification of the esters of formula I wherein $R_1$ is alkyl of 1 to 5 carbon atoms.

Another process of the invention for the preparation of compounds of formula I wherein Z is -CH$_2$-CH- and $R_1$ is hydrogen comprises reacting an alkylthioamide of formula II with a compound of the formula $$\begin{array}{c} \text{O} \quad \text{Hal} \\ \| \quad | \\ \text{H—C—CH—CH}_2\text{—CH—COOR}_1' \\ \quad\quad\quad\quad\quad\quad | \\ \quad\quad\quad\quad\quad\quad \text{COOR}_1' \end{array} \quad \text{VI}$$

wherein $R_1'$ is alkyl of 1 to 5 carbon atoms and Hal is chlorine or bromine to obtain a compound of the formula

VII $$\begin{array}{c} \text{N}\text{——}\text{CH} \\ \| \quad\quad \| \\ \text{R—C} \quad\quad \text{C—CH}_2\text{—CH—COOR}_1' \\ \diagdown\diagup \quad\quad\quad\quad | \\ \text{S} \quad\quad\quad\quad \text{COOR}_1' \end{array}$$

subjecting the latter to hydrolysis to form the corresponding acid of the formula

VIII $$\begin{array}{c} \text{N}\text{——}\text{CH} \\ \| \quad\quad \| \\ \text{R—C} \quad\quad \text{C—CH}_2\text{—CH—COOH} \\ \diagdown\diagup \quad\quad\quad\quad | \\ \text{S} \quad\quad\quad\quad \text{COOH} \end{array}$$

and decarboxylating the latter with a strong acid to obtain the corresponding compound of formula I wherein $R_1$ is hydrogen and Z is -CH$_2$-CH$_2$-.

The preferred conditions for the said reaction comprise reacting the compounds of formulae II and VI in an organic solvent such as dichloroethane, benzene, toluene, tetrahydrofuran or ethyl ether at reflux temperatures. The hydrolysis of the ester of formula VII is effected in the presence of a strong base such as alkali metal hydroxides like sodium hydroxide or potassium hydroxide. The strong acid for the decarboxylation step may be hydrochloric acid, sulfuric acid or phosphoric acid, for example, and the reaction is preferably effected in a hot aqueous media.

The compounds of formula I wherein Z is -CH$_2$-CH$_2$ or -(CH$_2$)$_4$- may also be prepared by reducing the corresponding compound of formula I wherein Z is -CH=CH- or -CH=CH-CH=CH- to obtain the corresponding saturated compound of formula I. The reduction is preferably effected with hydrogen in the presence of a catalyst such as palladized carbon and is effected in an organic solvent such as ethanol.

The compounds of formula I are useful intermediates for the preparation of the corresponding thiazole alkanols of the formula $$\begin{array}{c} \text{N}\text{——}\text{CH} \\ \| \quad\quad \| \\ \text{R—C} \quad\quad \text{C—(CH}_2\text{)}_n\text{—OH} \\ \diagdown\diagup \\ \text{S} \end{array}$$

wherein R has the above definition and n is an integer from 2 to 7 by reducing the compound of formula I with a mixed hydride as described in our copending, commonly assigned application Ser. No. 654,629 filed on even date herewith entitled Novel 5-Thiazole Alkanols which products also possess antilipolytic activity and are further useful as intermediates for the preparation of thiazole alkane carbamates of the formula $$\begin{array}{c} \text{N}\text{——}\text{CH} \quad\quad\quad \text{O} \\ \| \quad\quad \| \quad\quad\quad\quad \| \\ \text{R—C} \quad\quad \text{C—(CH}_2\text{)}_n\text{—O—C—R}_1 \\ \diagdown\diagup \\ \text{S} \end{array}$$

wherein R and n have the above definition and $R_1$ is -NH$_2$, -NHAlK, -NAlK$_2$, phenylamino or diphenylamino also possessing antilipolytic activity as described in our copending, commonly assigned application Ser. No. 654,630 filed on even date herewith entitled Novel Thiazole Derivatives. The compounds of formula I and their non-toxic, pharmaceutically acceptable acid addition salts also possess antilipolytic activity and reduce the level of free plasmatic fatty acids in the blood.

The novel intermediate products of the invention include 3-propyl-5-thiazole carboxaldehyde and its acid addition salts with a strong mineral or organic acid; the esters of formula VI; and the diacids and diesters of formula VII and VIII as well as their acid addition salts with a strong mineral or organic acid and the $NH_4$, alkali metal, alkaline earth metal and aluminum salts of the acids of formula VIII.

The starting compounds of formula II may be prepared by the process of Gilbert et al [Chem. Ab., Vol. 65, 20020e and ethyl 3-bromo-4-oxo-butyrate used in Example 7 is described in Helv. Chim. Acta., Vol. 33 (1950), p. 503–505 and the other products of formula III wherein Hal is bromine may be made by the same process by reacting a compound of the formula

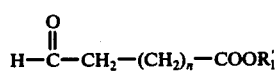

A with bromine in an organic solvent. The compounds of formula III in which Hal is chlorine may be formed by introducing chlorine gas into an organic solution of a compound of formula A. The compounds of formula A that are not known may be prepared by hydrolysis of the known esters followed by reesterification. 2-methyl-5-thiazole-carboxaldehyde and its preparation are described in Chem. Ab., Vol. 48 (1954), 2045 g and Chem. Ab., Vol. 62 (1965), 7764d. The compounds of formula IV that are not known may be prepared by oxidizing the corresponding alcohol with an oxidation agent such as manganese dioxide preferably in an organic solvent such as benzene, toluene or chloroform.

Ehtyl diethylphosphonocrotonate is described and prepared in J. Org. Chem., Vol. 32(1)(1967), p. 177–180. Other compounds of formula V which are not known may be prepared by reacting a trialkylphosphite with an alkyl bromocrotonate or alkyl chlorocrotonate as described in the said J. Org. Chem. article. The alkyl bromocrotonates may be prepared as described in Chem. Ab., Vol. 41 (1947), p. 3045. The alkyl chlorocrotonates may be prepared by reacting the alkyl crotonate in an organic solvent with a chlorinating agent such as N-chlorosuccinimide.

The compounds of formula VI may be prepared by reacting a diester of the formula

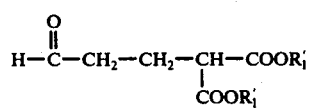

B in an organic solvent with bromine or with chlorine gas. The said diesters of formula B may be prepared by reaction with malonic acid derivatives and acrolein as described in J.A.C.S., Vol. 70, p. 3470 for γ,γ-dicarbethoxybutyraldehyde.

The novel hypolipemiant compositions of the invention are comprised of an effective amount of at least one compound of formula I and their non-toxic, pharmaceutically acceptable acid addition salts and a pharmaceutical carrier. Particularly active are the compounds of formula 1 wherein Z is -CH=CH-, -CH=CH-CH=CH- or a saturated alkylene with an even number of carbon atoms. The compositions may be in the form of tablets, dragees, gelules, granules, suppositories or injectable solutions or suspensions prepared in the usual manner.

The compositions contain the usual pharmaceutical excipients such as talc, arabic gum, lactose, starch, magnesium stearate, cacao butter, aqueous or non-aqueous vehicles, fatty bodies of animal or vegetable origin, paraffinic derivatives, glycols, diverse wetting agents, emulsifiers or dispersants or preservatives.

The compositions because of their antilipolytic activity are useful for the treatment of acute or chronic hyperlipemia, coronary insufficiencies, cardiac insufficiencies of atheromatosis origin and chronic anginia states.

The novel method of the invention for inducing hypolipemic activity in warm-blooded animals including humans comprises administering to warm-blooded animals a hypolipemically effective amount of at least one compound of formula I and their non-toxic, pharmaceutically acceptable acid addition salts. The compounds may be administered orally, rectally or parenterally. The usual useful daily dose is 2 to 50 mg/kg depending upon the particular compound and the method of administration.

In the following examples there are described several preferred embodiments to illustrate the invention. However, it is to be understood that the invention is not intended to be limited to the specific embodiments.

EXAMPLE 1

3-(2-methyl-5-thiazolyl)-2-propenoic acid

A mixture of 29 g of 2-methyl-5-thiazolecarboxaldehyde, 30 ml of pyridine, 29 g of malonic acid and 30 drops of piperidine was heated at 100°–100°C for 5 hours and was then returned to room temperature and poured into 500 ml of water. The pH of the solution was adjusted to 3 by addition of N sulfuric acid and the mixture was vacuum filtered. The recovered precipitate was dried to obtain 27.8 g of 3-(2-methyl-5-thiazolyl)-2-propenoic acid which was crystallized from 800 ml of ethanol containing 10% ethanol to obtain 23.8 of the said product melting at 204°C.

Analysis: $C_7H_7NO_2S$
Calculated: %C 49.68 %H 4.17 %N 8.28 %S 18.94
Found: 49.8 4.1 7.9 19.1.

EXAMPLE 2

2-methyl-5-thiazolepropanoic acid

STEP A: α-bromo-γ,γ-dicarbethoxy-butyraldehyde 2 ml of bromine were added dropwise with stirring at 20°C to a mixture of 150 g of γ,γ-dicarbethoxy-butyraldehyde [J.A.C.S., Vol. 70, p. 3470], 900 ml of anhydrous ethyl ether and 8.5 ml of dioxane and after cooling the mixture to 5°C, 33.5 ml of bromine were added dropwise thereto. The mixture was added to an aqueous solution saturated with sodium carbonate and the mixture was decanted. The ether phase was washed with water, was dried, filtered and evaporated to dryness to obtain 207 g of a brown oil which was rectified under reduced pressure to obtain 171 g or α-bromo-γ,γ-dicarbethoxy-butyraldehyde with a boiling point of 108°C at 0.02 mm Hg.

STEP B: diethyl 2-(2-methyl-5-thiazolyl-methyl)-propanedioate

A mixture of 108 g of α-bromo-γ,γ-dicarbethoxy-butyraldehyde 300 ml of anhydrous dichloroethane and 27 g of thioacetamide was refluxed for 6 hours during which 200 ml of dichloroethane were slowly distilled and the same quantity of dichloroethane was added again to the mixture. The mixture was cooled to room temperature and 500 ml of ice water were added thereto. Concentrated ammonium hydroxide solution was added to the mixture to adjust the pH to 10–12 and the mixture was decanted. The aqueous phase was extracted with methylene chloride and the organic extracts were dried over magnesium sulfate, filtered and evaporated to dryness to obtain 110 g of diethyl 2-(2-methyl-5-thiazolyl-methyl)-propanedioate. A sample of the product was rectified to obtain the product with a boiling point of 102°C at 0.02 mm Hg.

STEP C: 2-methyl-5-thiazolepropanoic acid

A mixture of 110 g of the product of Step C and 250 ml of 4N sodium hydroxide solution was stirred at room temperature for 16 hours and was then filtered. The filtrate was washed with ethyl acetate and the organic phase was re-extracted with water. The combined aqueous phases which contained 2-(2-methyl-5-thiazolyl-methyl)-propanedioic acid were treated with 100 ml of concentrated hydrochloric acid to obtain a pH of 1 and was refluxed for 5 hours and then returned to room temperature and iced. Concentrated ammonium hydroxide solution was added to adjust the pH of the mixture to 10–12 and then sulfur dioxide was bubbled through the mixture until the pH was 4–5. The mixture was saturated with sodium chloride and was extracted with ethyl acetate. The organic extracts were dried over magnesium sulfate, were filtered and evaporated to dryness to obtain 43 g of crystalline product which were crystallized from ethyl acetate to obtain 29 g of 2-methyl-5-thiazole-propanoic acid melting at 130°C.

Analysis: $C_7H_9NO_2S$
Calculated: %C 49.0 %H 5.30 %N 8.18 %S 18.73
Found: 49.1 5.3 7.9 18.3.

EXAMPLE 3

2-methyl-5-thiazolepropanoic acid

Hydrogen was passed for one hour through a mixture of 10 g of 3-(2-methyl-5-thiazolyl)-2-propanoic acid, 260 ml of methanol, 15 ml of triethylamine and 5 g of activated carbon with 10% palladium and the mixture was filtered. The filter was washed with ethanol and the filtrate was concentrated to dryness to obtain 13.3 g of a colorless oil which was dissolved in 100 ml of water. Sulfur dioxide was bubbled through the solution until the pH was acidic and excess sulfur dioxide was removed by bubbling nitrogen through the solution. The mixture was vacuum filtered and the recovered crystals were washed with water and dried to obtain 7.1 g of crystalline product which was crystallized fromethyl acetate to obtain 6.5 g of 2-methyl-5-thiazole-propanoic acid melting at 120°C.

Analysis: $C_7H_9NO_2S$
Calculated: %C 49.10 %H 5.30 %N 8.18 %S 18.73
Found: 49.1 5.2 8.0 18.6.

EXAMPLE 4

5-(2-methyl-5-thiazolyl)-2,4-pentadienoic acid

A solution of 12.5 g of ethyl diethylphosphonocrotonate in 25 ml of tetrahydrofuran was added with stirring to a mixture of 100 ml of anhydrous tetrahydrofuran and 3 g of sodium hydride in 46% of an oil cooled to 0°C and the mixture was stirred for 30 minutes at 0°C. Then, a mixture of 6.4 g of 2-methyl-5-thiazolecarboxaldehyde in 25 ml of tetrahydrofuran was added to the mixture at 0°C and 250 ml of ice and 250 250 ml of water were added. The mixture was extracted with methylene chloride and the organic extracts were washed with water, dried and filtered. The filtrate was evaporated to dryness under reduced pressure to obtain 13 g of raw product which was dissolved in ether and the ether solution was stirred in the presence of Florosil and then with activated carbon. The mixture was filtered and the filtrate was evaporated to dryness under reduced pressure to obtain 11 g of ethyl 5-(2-methyl-5-thiazolyl)-2,4-pentadienoate in the form of a pale yellow oil.

A mixture of 11 g of the said product and 100 ml of 1N potassium hydroxide in solution in ethanol was stirred for 90 minutes at room temperature and was then evaporated to dryness. The residue was dissolved in water and the aqueous phase was washed with ether. Sulfur dioxide was bubbled through the solution and the mixture was vacuum filtered. The recovered crystals were washed with water and dried to obtain 4.2 g of 5-(2-methyl-5-thiazolyl)-2,4-pentadienoic acid melting at 220°–222° C.

Analysis: $C_9H_9NO_2S$
Calculated: %C 55.37 %H 4.65 %N 7.17 %S 16.42
Found: 55.4 4.8 7.0 16.1.

EXAMPLE 5

2-methyl-5-thiazolepentanoic acid

Hydrogen was bubbled with stirring for 2 hours through a mixture of 4.2 g of 5-(2-methyl-5-thiazolyl)-2,4-pentadienoic acid, 200 ml of ethanol, 2 ml of triethylamine and 2 g of activated carbon containing 10% palladium and the mixture was filtered. The filter was washed with ethanol and the filtrate was evaporated to dryness. The residue was dissolved in 200 ml of water and the aqueous phase was washed with ether and extracted with ethyl acetate. The organic extracts were dried onver magnesium sulfate and were concentrated to dryness to obtain 4.2 g of product which was crystalized from isopropyl ether. The resulting 4 g of product were dissolved in 60 ml of ethyl acetate and a solution of N nitric acid in ethyl acetate was added thereto dropwise until the pH was 2–3. The mixture was vacuum filtered and the recovered crystals were dried and crystallized from isopropanol to obtain 3.4 g of the nitrate of 2-methyl-5-thiazole-pentanoic acid with a melting point of 102° C.

The product was dissolved in water containing sodium hydroxide and the solution was acidified by bubbling sulfur dioxide therethrough. The mixture was extracted with methylene chloride and the organic extracts was dried over magnesium sulfate, filtered and evaporated to dryness. The residue was crystallized from isopropyl ether to obtain 2.1 g of 2-methyl-5-thiazole-pentanoic acid melting at 75° C.

Analysis: $C_9H_{13}NO_2S$
Calculated: %C 54.25 %H 6.58 %N 7.03 %S 16.09
Found: 54.2 6.6 6.9 16.3.

EXAMPLE 6 ethyl 2-methyl-5-thiazole-acetate

A mixture of 28.7 g of ethyl 3-bromo-4-oxo-butyrate, 300 ml of dichloroethane and 11.2 g of thioacetamide was refluxed for 10 hours with stirring while replacing the dichloroethane that distilled to keep the volume constant and then the mixture was cooled to room temperature. The mixture was evaporated to dryness and the residue was dissolved in ethyl acetate. The solution was extracted with 2N hydrochloric acid and the pH of the aqueous extracts was made alkaline by addition of ammonium hydroxide. The mixture was extracted with ethyl acetate and the organic extract was washed with water, dried and evaporated to dryness to obtain 8.3 g of ethyl 2-methyl-5-thiazole acetate. The IR spectrum in $CHCl_3$ showed ester C=O at $1737^{cm-1}$ and C=C and C=N at $1535^{cm-1}$.

EXAMPLE 7

2-methyl-5-thiazole-acetic acid

A mixture of 2 g of ethyl 2-methyl-5-thiazole-acetate and a solution of 2 g of potassium hydroxide in 10 ml of methanol was stirred for 2 hours and was then evaporated to dryness. The residue was dissolved in water and sulfur dioxide was bubbled through the solution until the pH became acidic. The solution was saturated with sodium chloride and was then extracted with ethyl acetate. The organic extracts were washed with water, dried and evaporated to dryness to obtain 1.7 g of a yellow solid. The product was dissolved in methanol and the solution was treated with activated carbon, filtered and evaporated to dryness to obtain 1.7 g of raw product which was crystallized from isopropanol to obtain 1.4 g of 2-methyl-5-thiazole-acetic acid melting at 144°C.

Analysis: $C_6H_7NO_2S$
Calculated: %C 45.84 %H 4.48 %N 8.91 %S 20.39
Found: 45.6 4.5 8.6 20.6.

EXAMPLE 8 ethyl 2-propyl-5-thiazole-acetate

A mixture of 20.6 g of ethyl 2-bromo-4-oxo-butyrate, 10.9 g of thiobutyramide and 440 ml of dichloroethane was refluxed under a nitrogen atmosphere which recycling the dehydrated condensate. The mixture was cooled and then mixed with 45 ml of a saturated sodium bicarbonate aqueous solution. The mixture was decanted and the organic phase was dried and evaporated to dryness. The liquid residue was chromatographed over silica gel and elution with a 8-2 cyclohexane-benzene mixture yielded 15.4 g of ethyl 2-propyl-5-thiazole-acetate. The IR spectrum in $CHCl_3$ showed an ester carbonyl at $1737^{cm-1}$ and C=C at $1536^{cm-1}$

EXAMPLE 9

2-propyl-5-thiazole-acetic acid

A mixture of 2.13 g of ethyl 2-propyl-5-thiazole acetate, 11 ml of methanol and 1.1 ml of potassium hydroxide was stirred for 1 hour under a nitrogen atmosphere at room temperature and the methanol was distilled under reduced pressure. The residue was dissolved in 5 ml of water and 2 ml of concentrated hydrochloric acid and then 2.1 g of sodium acetate were added thereto. The mixture was extracted with methylene chloride and the organic extracts were dried and evaporated to dryness. The residue was crystallized from toluene to obtain 1.24g of 2-propyl-5-thiazole-acetic acid melting at 95° C.

Analysis: $C_8H_{11}NO_2S$
Calculated: %C 51.87 %H 5.98 %N 7.56 %S 17.31
Found: 52.0 6.0 7.3 17.4.

EXAMPLE 10 ethyl 5-(2-propyl-5-thiazolyl)-2,4-pentadienoate

Using the procedure of Example 4, 2-propyl-5-carboxaldehyde [prepared by reaction of manganese dioxide and 2-propyl-5-hydroxymethyl-thiazole in benzene] and ethyl diethylphosphonocrotonate were reacted to obtain ethyl 5-(2-propyl-5-thiazolyl)-2,4-pentadienoate melting at 52°C.

Analysis: $C_{11}H_{13}NO_2S$
Calculated: %C 62.12 %H 6.82 %N 5.57 %S 12.76
Found: 62.3 7.1 5.5 12.8.

EXAMPLE 11

Hemi-α,β-ethane disulfonate of 2propyl-5-thiazole-pentanoic acid

Using the procedure of Example 10, ethyl 5-(2-propyl-5-thiazolyl)2,4-pentadienoate was reacted with hydrogen in the presence of activated carbon containing 10% palladium and the resulting product was saponified to obtain 2-propyl-5-thiazole-pentanoic acid. The latter product was reacted with α,β-ethanedisulfonic acid to obtain the hemi-α,β-ethane disulfonate of 2-propyl-5-thiazole-pentanoic acid melting at 124°C.

| Analysis: $C_{12}H_{20}NO_5S_2$ | | | | |
|---|---|---|---|---|
| Calculated: | %C 44.70 | %H 6.25 | %N 4.34 | %S 19.84 |
| Found: | 44.9 | 6.2 | 4.3 | 19.8 |

EXAMPLE 12

Tablets were prepared containing 300 mg of 2-methyl-5-thiazole-propanoic acid and sufficient excipient consisting of lactose, wheat starch, rice starch, treated starch, talc and magnesium stearate. Gelules were prepared containing 300 mg of 2-methyl-5-thiazole-pentanoic acid and sufficient excipient consisting of talc, magnesium stearate and aerosil to obtain a final weight of 350 ml.

PHARMACOLOGICAL DATA

A. Acute toxicity

The acute toxicity was determined on groups of 10 mice weighing between 18 to 22 g and the product was administered intraperitoneally as a suspension in carboxymethylcellulose. The animals were observed for one week and the average lethal dose ($DL_{50}$) found is reported in Table I.

TABLE I

| Product of Examples | $DL_{50}$ in mg/kg |
|---|---|
| 1 | > 1000 |
| 2 | ≃ 600 |
| 5 | ≃ 500 |

B. Antilipolytic Activity

Male rats of the Sprague Dawley SPF strain weighing about 180 to 200 g were starved for 24 hours and then were given the test product orally. One hour after the oral administration, the animals were killed by carotidienne section and samples of the blood were obtained to determine the dosage of free fatty acids. The extraction of the free fatty acids was made by the technique of Dole [J. Clin. Invest., Vol. 38 (1959), p.

1544–1554] as modified by Trout et al [J. Lipid. Res., Vol. 1 (1960) p. 199-202]. The plasmatic extract free of phospholipids was colorimetrically determined by the method of Anthonis [J. Lipid. Res., Vol. 6 (1965), p. 307-312]. Under these test conditions, the dose which reduced by 50% the level of free fatty acids in the treated animals as compared to the controls ($DA_{50}$) found are reported in Table II.

TABLE II

| Product of Example | $DA_{50}$ in mg/kg |
|---|---|
| 1 | ≃ 5 |
| 2 | ≃ 1.5 |
| 5 | ≃ 5 |

The tested products shows a clear antilipolytic activity.

various modifications of the products and methods of the invention may be made without departing from the spirit or scope thereof and it is to be understood that the invention is intended to be limited only as defined in the appended claims.

We claim:

1. A compound selected from the group consisting of thiazoles of the formula $$R-C\underset{S}{\overset{N=CH}{\underset{\diagdown\;\;\diagup}{C}}}-Z-COOR_1$$

wherein R is alkyl of 1 to 5 carbon atoms, Z is selected from the group consisting of -CH=CH-, -CH=CH-CH=CH- and $-(CH_2)_n-$, n is an integer of 2, 4, or 6 and $R_1$ is selected from the group consisting of hydrogen, alkyl of 1 to 5 carbon atoms, $-NH_4$ and alkali metal, alkaline earth metal and aluminum cations and the non-toxic, pharmaceutically acceptable acid addition salts.

2. A compound of claim 1 wherein Z is $-(CM_2)_2-$ or $-(CH_2)_4-$.

3. A compound of claim 1 which is 2-methyl-5-thiazole-propanoic acid and its non-toxic, pharmaceutically acceptable acid addition salts.

4. A compound of claim 1 which is 3-(2-methyl-5-thiazolyl)-2-propenoic acid and its non-toxic, pharmaceutically acceptable acid addition salts.

5. A compound of claim 1 which is 2-methyl-5-thiazolepentanoic acid and its non-toxic, pharmaceutically acceptable acid addition salts.

6. A compound of claim 1 which is 5-(2-methyl-5-thiazolyl)-2,4-pentadienoic acid and its non-toxic, pharmaceutically acceptable acid addition salts.

7. A compound of claim 1 which is ethyl 5-(2-propyl-5-thiazolyl)-2,4-pentadienoate and its non-toxic, pharmaceutically acceptable acid addition salts.

8. A compound of claim 1 which is 2-propyl-5-thiazolepentanoic acid and its non-toxic, pharmaceutically acceptable acid addition salts.

9. The compound of claim 8 wherein the acid salt is the hemi-α,β-ethanedisulfonate.

10. A hypolipemiant composition comprising an effective amount of at least one compound of claim 1 and a pharmaceutical carrier.

11. A method of inducing hypolipemic activity in warm-blooded animals comprising administering to warm-blooded animals an hypolipemically effective amount of at least one compound of claim 1.

12. The method of claim 11 wherein Z is $-CH_2-CH_2-$ or $-(CH_2)_4-$.

13. The method of claim 11 wherein the compound is 2-methyl-5-thiazole-propanoic acid.

14. The method of claim 11 wherein the compound is 3-(2-methyl-5-thiazolyl)-2-propenoic acid.

15. The method of claim 11 wherein the compound is 2-methyl-5-thiazole-pentanoic acid.

* * * * *

UNITED STATES PATENT OFFICE
CERTIFICATE OF CORRECTION

Patent No. 4,053,618     Dated Oct. 11, 1977

Inventor(s) ANDRE POITTEVIN and VESPERTO TORELLI

It is certified that error appears in the above-identified patent and that said Letters Patent are hereby corrected as shown below:

| Col. | Line | | | |
|------|------|---|---|---|
| [73] | | Assignee | | |
| | | "UCLAF" should be --Uclaf-- | | |
| [57] | | Abstract formula | | |

"
$$\begin{matrix} N & \!\!\!\!\text{---} & CH \\ \| & & \| \\ C & & C\text{-}Z\text{-}COOR_1 \\ & \diagdown \;\; S \;\; \diagup & \end{matrix}$$
" should be $$\begin{matrix} \text{--}N & \!\!\!\!\text{---} & CH & \text{--} \\ \| & & \| \\ R\text{---}C & & C\text{-}Z\text{-}COOR_1 \\ & \diagdown \;\; S \;\; \diagup & \end{matrix}$$

| Col. | Line | | | |
|------|------|---|---|---|
| 1 | 50 | " " " " " " " " " | | |
| 2 | 16 | 3 | 28 | "-C=CH-CH=CH" should be -- -CH=CH-CH=CH- -- |

UNITED STATES PATENT OFFICE
CERTIFICATE OF CORRECTION

Patent No. 4,053,618  Dated Oct. 11, 1977

Inventor(s) ANDRE POITTEVIN and VESPERTO TORELLI

It is certified that error appears in the above-identified patent and that said Letters Patent are hereby corrected as shown below:

| Col. | Line | |
|------|------|---|
| 3 | 54 | "$-CH_2-CH-$" should be -- $-CH_2-CH_2-$ -- |
| 3 | 68 | "VII" should be next to the formula |
| 7 | 53 | "fromethyl" should be --from ethyl-- |
| 8 | 1 | Cancel one of "250" |
| 9 | 41 | "440ml" should be --400 ml-- |
| 10 | 6 | "2-propyl-5-car should be -- -2-propyl-5-thiazole-carboxaldehyde-- |
| 11 | 20 | "various" should be --Various-- |
| 12 | Claim 2, 3 | "$-(CM_2)_2$" should be --$(CH_2)_2$-- |

Signed and Sealed this

Twenty-first Day of February 1978

[SEAL]

Attest:

RUTH C. MASON  
Attesting Officer

LUTRELLE F. PARKER  
Acting Commissioner of Patents and Trademarks